US008337825B2

(12) United States Patent
Kungl et al.

(10) Patent No.: US 8,337,825 B2
(45) Date of Patent: Dec. 25, 2012

(54) GLYCOSAMINOGLYCAN-ANTAGONISING MCP-1 MUTANTS

(75) Inventors: Andreas Kungl, Graz (AT); Anna Maria Piccinini, London (GB); Christian Weber, Aachen (DE)

(73) Assignee: Protaffin Biotechnologie AG, Graz (AT)

( * ) Notice: Subject to any disclaimer, the term of this patent is extended or adjusted under 35 U.S.C. 154(b) by 130 days.

(21) Appl. No.: 12/670,378

(22) PCT Filed: Jul. 21, 2008

(86) PCT No.: PCT/EP2008/006298
§ 371 (c)(1),
(2), (4) Date: Jan. 22, 2010

(87) PCT Pub. No.: WO2009/015884
PCT Pub. Date: Feb. 5, 2009

(65) Prior Publication Data

US 2010/0197583 A1 Aug. 5, 2010

Related U.S. Application Data

(60) Provisional application No. 60/953,140, filed on Jul. 31, 2007.

(30) Foreign Application Priority Data

Sep. 27, 2007 (EP) .................................... 07450166

(51) Int. Cl.
*A61K 38/19* (2006.01)
*C07K 14/52* (2006.01)

(52) U.S. Cl. ...................................... 424/85.1; 530/324

(58) Field of Classification Search ........................ None
See application file for complete search history.

(56) References Cited

U.S. PATENT DOCUMENTS 6,107,565 A 8/2000 O'Rourke
2003/0162737 A1 8/2003 Egashira

FOREIGN PATENT DOCUMENTS

WO WO 03/084993 A1 10/2003
WO WO 2005/054285 A 6/2005

OTHER PUBLICATIONS

Mikayama et al. Proc. Natl. Acad. Sci. USA, vol. 90, pp. 10056-10060 (1993).*
Voet et al. Biochemistry John Wiley & Sons, Inc., pp. 126-128 and 228-234 (1990).*
Jarnagin, Kurt et al., : "Identification of surface residues of the monocyte chemotactic protein 1 that affect signaling through the receptor CCR2," Biochemistry, American Chemical Society, Easton, PA, vol. 38, No. 49, Dec. 7, 1999, pp. 16167-16177.
International Preliminary Report on Patentability, PCT/EP2008/006298, Jul. 27, 2009.
International Search Report, PCT/EP2008/006298, Feb. 5, 2009.
Steitz, S.A., et al., "Mapping of MCP-1 functional domains by peptise analysis and site-directed mutagenesis," FEBS Letters, vol. 430, No. 3, Jul. 3, 1998, pp. 158-164.
Paavola, Chad, et al. "Monomeric monocyte chemoattractant protein-1 {MCP-1) binds and activates the MCP-1 receptor CCR2B," Journal of Biological Chemistry, vol. 273, No. 50, Dec. 11, 1998, pp. 33157-33165.
Potzinger, H., et al., : "Developing chemokine mutants with improved proteoglycan affinity and knocked-out GPCR activity as anti-inflammatory recombinant drugs," Biochemical Society Transactions, vol. 34, No. 3, Jun. 2006, pp. 435-437.
Gesslbauer, Bernd et al., : "Glycomic approaches toward drug development: therapeutically exploring the glycosaminoglycanome," Current Opinion in Molecular Therapeutics, vol. 8, No. 6, Dec. 2006, pp. 521-528.
Lau, Elaine, K., et al., "Identification of the glycosaminoglycan binding site of the CC chemokine, MCP-1—Implications for structure and function in vivo," Journal of Biological Chemistry, vol. 279, No. 21, May 21, 2004, pp. 22294-22305.
Hemmerich, Stefan, et al., "Identification of residues in the monocyte chemotactic protein-I that contact the MCP-I receptor, CCR2," Biochemistrym vol. 38, No. 40, Oct. 5, 1999, pp. 13013-13025.
Protaffin Biotechnologie AG, "CellJammerTM discovery technology" [Online] Sep. 7, 2007.
Alcami A .et al., J. Immunol. 160, 2, pp. 624-33, 1998.
Baggiolini M., J. Int. Med. 250, pp. 91-104, 2001.
Gupta S.K. et al., Proc.Natl.Acad.Sci., USA 92, (17), pp. 7799-7803, 1995.
Ali S. et al., Biochem. J. 358, pp. 737-745, 2001.
Nelken N. A et al., J. Clin. Invest 88, pp. 1121-1127, 1991.
Yla-Herttuala S., Proc. Natl. Acad. Sci, USA 88, pp. 5252-5256, 1991.
Koch A. E. et al., J. Clin Invest. 90, pp. 772-779, 1992.
Hosaka S. et al., Clin. Exp. Immunol. 97, 3, pp. 451-457, 1994.
Robinson E. et al., Clin Exp. Immunol. 101, 3, pp. 398-407, 1995.
MacDermott R. P. et al., J. Clin. Immunol. 19, pp. 266-272, 1999.
Aukrust P., et al. Circulation 97, pp. 1136-1143, 1998.
Hohensinner P. J., et al., FEBS Letters 580, pp. 3532-3538, 2006.
Grewal I. S. et al., J. Immunol. 159, 1, pp. 401-408, 1997.
Lukacs N. W. et al., J. Immunol. 158, 9, pp. 4398-4404, 1997. Flory C. M. et al., 1. Lab Invest. 69, 4, pp. 396-404, 1993.
Gong J. H. et al., J. Exp. Med. 186, 1, pp. 131-137, 1997.
Boring L., et al., J. Biol. Chem. 271, 13, pp. 7551-7558, 1996.
Kuziel W.A. et al., Proc. Natl. Acad. Sci. USA 94, 22, pp. 12053-12058, 1997.
Lu B. et al., J. Exp. Med. 187, 4, pp. 601-608, 1998.
Zisman D. A. et al., J. Clin. Invest 99, 12, pp. 2832-2836, 1997.
Gosling J. et al., J. Clin Invest 103, 6, pp. 773-738, 1999.

* cited by examiner

*Primary Examiner* — Prema Mertz
(74) *Attorney, Agent, or Firm* — Michael Fedrick; Loza & Loza, LLP

(57) ABSTRACT

Novel mutants of human monocyte chemoattractant protein 1 (MCP-1) with increased glycosaminoglycan (GAG) binding affinity and knocked-out or reduced GPCR activity compared to wild type MCP-1, and their use for therapeutic treatment of inflammatory diseases.

15 Claims, 9 Drawing Sheets

Fig. 1 wtMCP1

Figure 2A:
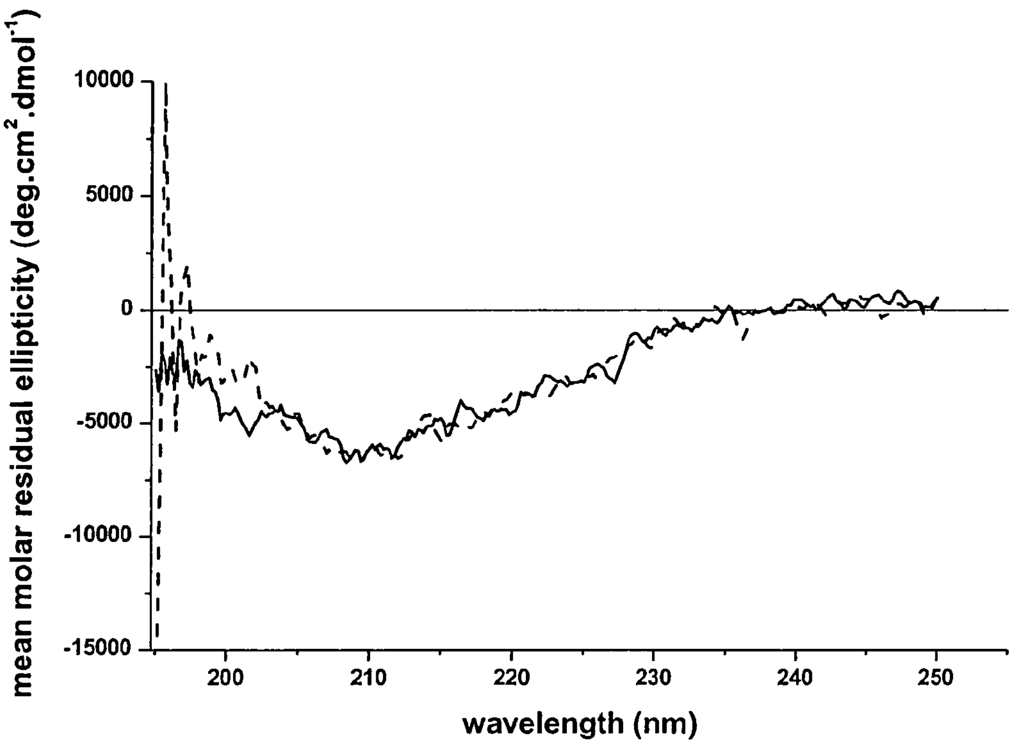

QPDAINAPVTCCYNFTNRKISVQRLASYRRITSSKCPKEAVIFKTIVAKEICADPKQKWVQDSMDHLDKQTQTPKT (SEQ ID. NO 1)

Met-MCP-1

MQPDAINAPVTCCYNFTNRKISVQRLASYRRITSSKCPKEAVIFKTIVAKEICADPKQKWVQDSMDHLDKQTQTPKT (SEQ ID. NO 2)

Met-MCP-1 Y13A S21K

MQPDAINAPVTCCANFTNRKIKVQRLASYRRITSSKCPKEAVIFKTIVAKEICADPKQKWVQDSMDHLDKQTQTPKT (SEQ ID. NO 3)

Met-MCP-1 Y13A S21K V47K

MQPDAINAPVTCCANFTNRKIKVQRLASYRRITSSKCPKEAVIFKTIKAKEICADPKQKWVQDSMDHLDKQTQTPKT (SEQ ID. NO 4)

Met-MCP-1 Y13A S21K Q23R

MQPDAINAPVTCCANFTNRKIKVRRLASYRRITSSKCPKEAVIFKTIVAKEICADPKQKWVQDSMDHLDKQTQTPKT (SEQ ID. NO 5)

Met-MCP-1 Y13A S21K Q23R V47K

MQPDAINAPVTCCANFTNRKIKVRRLASYRRITSSKCPKEAVIFKTIKAKEICADPKQKWVQDSMDHLDKQTQTPKT (SEQ ID. NO 6)

Control P008

MCP-1 Y13AS21KV47K

ATGCAACCGGACGCTATCAACGCACCGGTTACTTGTTGTGCGAACTTCACCAACCGT
AAGATCAAAGTTCAGCGTCTGGCTAGCTACCGTCGTATCACGAGCTCTAAATGCCCG
AAAGAAGCTGTTATCTTCAAAACCATCAAAGCTAAAGAAATCTGCGCGGATCCGAAAC
AGAAATGGGTTCAGGACTCTATCGACCACCTGGACAAACAGACCCAGACCCCGAAGA
CCTGA
(SEQ ID No. 7)

MCP-1 Y13AS21KQ23R

ATGCAACCGGACGCTATCAACGCACCGGTTACTTGTTGTGCGAACTTCACCAACCGT
AAGATCAAAGTTCGCCGTCTGGCTAGCTACCGTCGTATCACGAGCTCTAAATGCCCG
AAAGAAGCTGTTATCTTCAAAACCATCGTTGCTAAAGAAATCTGCGCGGATCCGAAAC
AGAAATGGGTTCAGGACTCTATCGACCACCTGGACAAACAGACCCAGACCCCGAAGA
CCTGA
(SEQ ID No. 8)

MCP-1 Y13AS21KQ23RV47K

ATGCAACCGGACGCTATCAACGCACCGGTTACTTGTTGTGCGAACTTCACCAACCGT
AAGATCAAAGTTCGCCGTCTGGCTAGCTACCGTCGTATCACGAGCTCTAAATGCCCG
AAAGAAGCTGTTATCTTCAAAACCATCAAAGCTAAAGAAATCTGCGCGGATCCGAAAC
AGAAATGGGTTCAGGACTCTATCGACCACCTGGACAAACAGACCCAGACCCCGAAGA
CCTGA
(SEQ ID No. 9)

Fig. 9

SEQUENCE LISTING

```
<160> NUMBER OF SEQ ID NOS: 10

<210> SEQ ID NO 1
<211> LENGTH: 76
<212> TYPE: PRT
<213> ORGANISM: Homo sapiens

<400> SEQUENCE: 1

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75


<210> SEQ ID NO 2
<211> LENGTH: 77
<212> TYPE: PRT
<213> ORGANISM: Artificial
<220> FEATURE:
<223> OTHER INFORMATION: modified MCP-1 protein

<400> SEQUENCE: 2

Met Gln Pro Asp Ala Ile Asn Ala Pro Val Thr Cys Cys Tyr Asn Phe
1               5                   10                  15

Thr Asn Arg Lys Ile Ser Val Gln Arg Leu Ala Ser Tyr Arg Arg Ile
            20                  25                  30
```

-continued

Thr Ser Ser Lys Cys Pro Lys Glu Ala Val Ile Phe Lys Thr Ile Val
35 40 45

Ala Lys Glu Ile Cys Ala Asp Pro Lys Gln Lys Trp Val Gln Asp Ser
50 55 60

Met Asp His Leu Asp Lys Gln Thr Gln Thr Pro Lys Thr
65 70 75

<210> SEQ ID NO 3
<211> LENGTH: 77
<212> TYPE: PRT
<213> ORGANISM: Artificial
<220> FEATURE:
<223> OTHER INFORMATION: modified MCP-1 protein

<400> SEQUENCE: 3

Met Gln Pro Asp Ala Ile Asn Ala Pro Val Thr Cys Cys Ala Asn Phe
1 5 10 15

Thr Asn Arg Lys Ile Lys Val Gln Arg Leu Ala Ser Tyr Arg Arg Ile
20 25 30

Thr Ser Ser Lys Cys Pro Lys Glu Ala Val Ile Phe Lys Thr Ile Val
35 40 45

Ala Lys Glu Ile Cys Ala Asp Pro Lys Gln Lys Trp Val Gln Asp Ser
50 55 60

Met Asp His Leu Asp Lys Gln Thr Gln Thr Pro Lys Thr
65 70 75

<210> SEQ ID NO 4
<211> LENGTH: 77
<212> TYPE: PRT
<213> ORGANISM: Artificial
<220> FEATURE:
<223> OTHER INFORMATION: modified MCP-1 protein

<400> SEQUENCE: 4

Met Gln Pro Asp Ala Ile Asn Ala Pro Val Thr Cys Cys Ala Asn Phe
1 5 10 15

Thr Asn Arg Lys Ile Lys Val Gln Arg Leu Ala Ser Tyr Arg Arg Ile
20 25 30

Thr Ser Ser Lys Cys Pro Lys Glu Ala Val Ile Phe Lys Thr Ile Lys
35 40 45

Ala Lys Glu Ile Cys Ala Asp Pro Lys Gln Lys Trp Val Gln Asp Ser
50 55 60

Met Asp His Leu Asp Lys Gln Thr Gln Thr Pro Lys Thr
65 70 75

<210> SEQ ID NO 5
<211> LENGTH: 77
<212> TYPE: PRT
<213> ORGANISM: Artificial
<220> FEATURE:
<223> OTHER INFORMATION: modified MCP-1 protein

<400> SEQUENCE: 5

Met Gln Pro Asp Ala Ile Asn Ala Pro Val Thr Cys Cys Ala Asn Phe
1 5 10 15

Thr Asn Arg Lys Ile Lys Val Arg Arg Leu Ala Ser Tyr Arg Arg Ile
20 25 30

Thr Ser Ser Lys Cys Pro Lys Glu Ala Val Ile Phe Lys Thr Ile Val
35 40 45

Ala Lys Glu Ile Cys Ala Asp Pro Lys Gln Lys Trp Val Gln Asp Ser
50 55 60

-continued

Met Asp His Leu Asp Lys Gln Thr Gln Thr Pro Lys Thr
65 70 75

<210> SEQ ID NO 6
<211> LENGTH: 77
<212> TYPE: PRT
<213> ORGANISM: Artificial
<220> FEATURE:
<223> OTHER INFORMATION: modified MCP-1 protein

<400> SEQUENCE: 6

Met Gln Pro Asp Ala Ile Asn Ala Pro Val Thr Cys Cys Ala Asn Phe
1 5 10 15

Thr Asn Arg Lys Ile Lys Val Arg Arg Leu Ala Ser Tyr Arg Arg Ile
20 25 30

Thr Ser Ser Lys Cys Pro Lys Glu Ala Val Ile Phe Lys Thr Ile Lys
35 40 45

Ala Lys Glu Ile Cys Ala Asp Pro Lys Gln Lys Trp Val Gln Asp Ser
50 55 60

Met Asp His Leu Asp Lys Gln Thr Gln Thr Pro Lys Thr
65 70 75

<210> SEQ ID NO 7
<211> LENGTH: 234
<212> TYPE: DNA
<213> ORGANISM: Artificial
<220> FEATURE:
<223> OTHER INFORMATION: nucleotide sequence of modified MCP-1 protein
Y13AS21KV47K

<400> SEQUENCE: 7
atgcaaccgg acgctatcaa cgcaccggtt acttgttgtg cgaacttcac caaccgtaag 60
atcaaagttc agcgtctggc tagctaccgt cgtatcacga gctctaaatg cccgaaagaa 120
gctgttatct tcaaaaccat caaagctaaa gaaatctgcg cggatccgaa acagaaatgg 180
gttcaggact ctatcgacca cctggacaaa cagacccaga ccccgaagac ctga 234

<210> SEQ ID NO 8
<211> LENGTH: 234
<212> TYPE: DNA
<213> ORGANISM: Artificial
<220> FEATURE:
<223> OTHER INFORMATION: nucleotide sequence of modified MCP-1 protein
Y13AS21KQ23R

<400> SEQUENCE: 8
atgcaaccgg acgctatcaa cgcaccggtt acttgttgtg cgaacttcac caaccgtaag 60
atcaaagttc gccgtctggc tagctaccgt cgtatcacga gctctaaatg cccgaaagaa 120
gctgttatct tcaaaaccat cgttgctaaa gaaatctgcg cggatccgaa acagaaatgg 180
gttcaggact ctatcgacca cctggacaaa cagacccaga ccccgaagac ctga 234

<210> SEQ ID NO 9
<211> LENGTH: 234
<212> TYPE: DNA
<213> ORGANISM: Artificial
<220> FEATURE:
<223> OTHER INFORMATION: nucleotide sequence of modified MCP-1 protein
Y13AS21KQ23RV47K

<400> SEQUENCE: 9
atgcaaccgg acgctatcaa cgcaccggtt acttgttgtg cgaacttcac caaccgtaag 60

-continued

```
atcaaagttc gccgtctggc tagctaccgt cgtatcacga gctctaaatg cccgaaagaa    120

gctgttatct tcaaaaccat caaagctaaa gaaatctgcg cggatccgaa acagaaatgg    180

gttcaggact ctatcgacca cctggacaaa cagacccaga ccccgaagac ctga          234


<210> SEQ ID NO 10
<211> LENGTH: 77
<212> TYPE: PRT
<213> ORGANISM: Artificial
<220> FEATURE:
<223> OTHER INFORMATION: mutated MCP-1 protein
<220> FEATURE:
<221> NAME/KEY: MISC_FEATURE
<222> LOCATION: (1)..(1)
<223> OTHER INFORMATION: M = M or no amino acid residue
<220> FEATURE:
<221> NAME/KEY: MISC_FEATURE
<222> LOCATION: (3)..(9)
<223> OTHER INFORMATION: PDAINAX = PDAINAX or no amino acid residue
<220> FEATURE:
<221> NAME/KEY: MISC_FEATURE
<222> LOCATION: (9)..(9)
<223> OTHER INFORMATION: Xaa is Pro, Ala, Gly or Leu
<220> FEATURE:
<221> NAME/KEY: MISC_FEATURE
<222> LOCATION: (14)..(14)
<223> OTHER INFORMATION: Xaa is Tyr or Ala
<220> FEATURE:
<221> NAME/KEY: MISC_FEATURE
<222> LOCATION: (19)..(19)
<223> OTHER INFORMATION: Xaa is Arg or Lys
<220> FEATURE:
<221> NAME/KEY: MISC_FEATURE
<222> LOCATION: (20)..(20)
<223> OTHER INFORMATION: Xaa is Arg or Lys
<220> FEATURE:
<221> NAME/KEY: MISC_FEATURE
<222> LOCATION: (22)..(22)
<223> OTHER INFORMATION: Xaa is Ser, Arg, Lys, His, Asn or Gln
<220> FEATURE:
<221> NAME/KEY: MISC_FEATURE
<222> LOCATION: (24)..(24)
<223> OTHER INFORMATION: Xaa is Arg, Lys, His, Asn or Gln
<220> FEATURE:
<221> NAME/KEY: MISC_FEATURE
<222> LOCATION: (48)..(48)
<223> OTHER INFORMATION: Xaa is Val, Arg, Lys, His, Asn or Gln

<400> SEQUENCE: 10

Met Gln Pro Asp Ala Ile Asn Ala Xaa Val Thr Cys Cys Xaa Asn Phe
1               5                   10                  15

Thr Asn Xaa Xaa Ile Xaa Val Xaa Arg Leu Ala Ser Tyr Arg Arg Ile
            20                  25                  30

Thr Ser Ser Lys Cys Pro Lys Glu Ala Val Ile Phe Lys Thr Ile Xaa
        35                  40                  45

Ala Lys Glu Ile Cys Ala Asp Pro Lys Gln Lys Trp Val Gln Asp Ser
    50                  55                  60

Met Asp His Leu Asp Lys Gln Thr Gln Thr Pro Lys Thr
65                  70                  75
```

GLYCOSAMINOGLYCAN-ANTAGONISING MCP-1 MUTANTS

CROSS-REFERENCE TO RELATED APPLICATIONS

This application is the U.S. national stage of International Patent Application No. PCT/EP2008/006298, filed on Jul. 31, 2008 and entitled GLYCOSAMINOGLYCAN-ANTAGONISING MCP-1 MUTANTS AND METHODS OF USING SAME, which claims the benefit of priority from U.S. Patent Application No. 60/953,140, filed on Jul. 31, 2007 and entitled GLYCOSAMINOGLYCAN-ANTAGONISING MCP-1 MUTANTS AND METHODS OF USING SAME, and from European Patent Application No. 07450166.9, filed on Sep. 27, 2007 and entitled GLYCOSAMINOGLYCAN-ANTAGONISING MCP-1 MUTANTS AND METHODS OF USING SAME. The disclosures of the foregoing applications are incorporated herein by reference in their entirety.

FIELD OF THE INVENTION

The present invention relates to novel mutants of human monocyte chemoattractant protein 1 (MCP-1) with increased glycosaminoglycan (GAG) binding affinity and knocked-out or reduced GPCR activity compared to wild type MCP-1, and to their use for therapeutic treatment of inflammatory diseases.

All chemokines, with the exception of lymphotactin and fraktaline/neurotactin which are members of the C and CX3C chemokine subfamily, respectively, have four cysteines in conserved positions and can be divided into the CXC or α-chemokine and the CC or β-chemokine subfamilies on the basis of the presence or absence, respectively, of an amino acid between the two cysteines within the N-terminus. Chemokines are small secreted proteins that function as intercellular messengers to orchestrate activation and migration of specific types of leukocytes from the lumen of blood vessels into tissues (Baggiolini M., J. Int. Med. 250, 91-104 (2001)). This event is mediated by the interaction of chemokines with seven transmembrane G-protein-coupled receptors (GPCRs) on the surface of target cells. Such interaction occurs in vivo under flow conditions. Therefore, the establishment of a local concentration gradient is required and ensured by the interaction of chemokines with cell surface glycosaminoglycans (GAGs). Chemokines have two major sites of interaction with their receptors, one in the N-terminal domain which functions as a triggering domain, and the other within the exposed loop after the second cysteine, which functions as a docking domain (Gupta S. K. et al., Proc. Natl. Acad. Sci., USA, 92, (17), 7799-7803 (1995)). The GAG binding sites of chemokines comprise clusters of basic amino acids spatially distinct (Ali S. et al., Biochem. J. 358, 737-745 (2001)). Some chemokines, such as RANTES, have the BBXB motif in the 40 s loop as major GAG binding site; IL-8 interacts with GAGs through the C-terminal α-helix and Lys 20 in the proximal N-loop. Other chemokines, such as MCP-1, show a significant overlap between the residues that comprise the receptor binding and the GAG binding site (Lau E. K. et al., J. Biol. Chem., 279 (21), 22294-22305 (2004)).

In the context of the chemokine-β family of cytokines, monocyte chemoattractant protein-1 (MCP-1) is a monocyte and lymphocyte-specific chemoattractant and activator found in a variety of diseases that feature a monocyte-rich inflammatory component, such as atherosclerosis (Nelken N. A. et al., J. Clin. Invest. 88, 1121-1127 (1991); Yla-Herttuala, S., Proc. Natl. Acad. Sci USA 88, 5252-5256 (1991), rheumatoid arthritis (Koch A. E. et al., J. Clin. Invest. 90, 772-779 (1992); Hosaka S. et al., Clin. Exp. Immunol. 97(3), 451-457 (1994), Robinson E. et al., Clin. Exp. Immunol. 101(3), 398-407 (1995)), inflammatory bowel disease (MacDermott R. P. et al., J. Clin. Immunol. 19, 266-272 (1999)) and congestive heart failure (Aukrust P., et al., Circulation 97, 1136-1143 (1998), Hohensinner P. J. et al., FEBS Letters 580, 3532-3538 (2006)). Crucially, knockout mice that lack MCP-1 or its receptor CCR2, are unable to recruit monocytes and T-cells to inflammatory lesions (Grewal I. S. et al., J. Immunol. 159 (1), 401-408 (1997), Boring L. et al., J. Biol. Chem. 271 (13), 7551-7558 (1996), Kuziel W. A., et al., Proc. Natl. Acad. Sci. USA 94 (22), 12053-8 (1997), Lu B., et al., J. Exp. Med. 187 (4), 601-8 (1998)); furthermore, treatment with MCP-1 neutralizing antibodies or other biological antagonists can reduce inflammation in several animal models (Lukacs N. W. et al., J. Immunol., 158 (9), 4398-4404 (1997), Flory C. M. et al., 1. Lab. Invest. 69 (4), 396-404 (1993), Gong J. H., et al., J. Exp. Med. 186 (1), 131-7 (1997), Zisman D. A. et al., J. Clin. Invest. 99 (12), 2832-6 (1997)). Finally, LDL-receptor/MCP-1-deficient and apoB-transgenic/MCP-1-deficient mice show considerably less lipid deposition and macrophage accumulation throughout their aortas compared to the WT MCP-1 strains (Alcami A. et al., J. Immunol. 160 (2), 624-33 (1998), Gosling J. et al., J. Clin. Invest. 103 (6), 773-8 (1999)).

Since the first chemokines and their receptors have been identified, the interest on exactly understanding their roles in normal and diseased physiology has become more and more intense. The constant need for new anti-inflammatory drugs with modes of action different from those of existing drugs support the development of new protein-based GAG-antagonists and their use in an inflammatory set.

Since in the last years the molecular basis of the interactions of MCP-1 with CCR2 and GAGs have been studied in great detail, targeted engineering of the chemokine towards becoming an effective antagonist of MCP-1's biological action is feasible.

For this purpose several recombinant MCP-1 variants that compete with their wild type counterpart for glycosaminoglycan binding and show reduced or knocked out activation of leukocytes have been generated.

Consequently, one subject matter of the present invention is to inhibit leukocyte, more specifically monocyte and T cell, migration by antagonizing the GAG interaction with an MCP-1-based mutant protein in the context of inflammatory or allergic processes.

The invention is based on engineering a higher GAG binding affinity into human MCP-1, either by modifying the wild type GAG binding region or by introducing a new GAG binding region into the MCP1 protein and simultaneously knocking out or reducing its GPCR activity, specifically the CCR2 activity of the chemokine. This has been successfully accomplished with a mutant MCP-1 protein wherein a region of the MCP-1 protein is modified in a structure conserving way by introducing basic and/or electron donating amino acids or replacing native amino acids with basic and/or electron donating amino acids and optionally also modifying the N-terminal region of said MCP-1 protein by addition, deletion and/or replacement of amino acids and, optionally, adding an N-terminal Methionine (M) to the mutant MCP-1 protein, resulting in partial or complete loss of chemotactic activity. Said inventive MCP-1 mutants can specifically exhibit a minimum five-fold improved Kd for standard GAGs (heparin or heparan sulfate) and they are deficient or reduced in inducing Calcium-release in standard monocytic cell culture.

MCP-1 mutant proteins showing increased GAG binding affinities and reduced GPCR activity has not been disclosed or indicated before. US2003/0162737 describes MCP-1 molecules with N-terminal deletions and replacements with amino acids N or L at selected positions 22 and 24 f the MCP-1 protein, yet these mutant proteins did not show the advantageous features of the inventive MCP-1 proteins. This was also not disclosed by Steitz S. et al (FEBS Letters, 40 (1998), pp. 158-164) who modified only positions 13 and 18 of the MCP-1 protein. Paavola C. et al. (J. Biol. Chem., 1998, 273, pp. 33157-33165) describe only MCP-1 mutants which are involved in receptor binding activity but did include modifications to reduce GAG binding affinity of the mutant MCP-1 protein.

Further, the present invention provides an isolated polynucleic acid molecule coding for the mutant MCP-1 protein of the invention, and a vector comprising an isolated DNA molecule coding for the mutant MCP-1 protein, and a recombinant cell transfected with the vector.

The mutant MCP-1 protein according to the present invention can also be formulated as a pharmaceutical composition comprising the mutant MCP-1 protein or a polynucleic acid molecule coding for MCP-1 mutant protein, a vector containing an isolated DNA molecule coding for the MCP-1 mutant protein, and a pharmaceutically acceptable carrier.

Said MCP-1 mutant protein or the polynucleotide coding therefor or the vector containing said polynucleotide can also be used for inhibiting or suppressing the biological activity of the respective wild type protein.

The inventive MCP-1 mutant protein according to the invention, a polynucleic acid coding therefor or a vector containing the polynucleotide can also be used in a method for preparing a medicament for the treatment of chronic or acute inflammatory diseases or allergic conditions. Preferably, the disease is selected from the group comprising rheumatoid arthritis, uveitis, inflammatory bowel disease, myocardial infarction, congested heart failure or ischemia reperfusion injury.

FIGURES

Figure 2B:
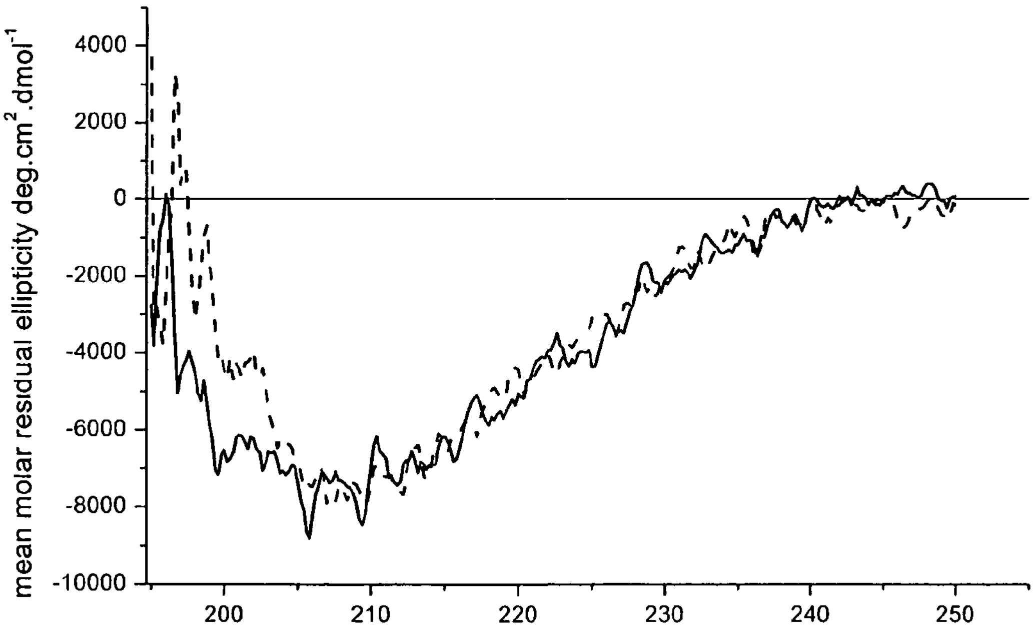

FIG. 1: Sequence of MCP-1 mutants, mutations with respect to the wild type chemokine are underlined FIG. 2: Structural change of wtMCP-1 (FIG. 2 *a*) and Met-MCP-1 Y13A S21K Q23R (FIG. 2*b*) upon heparan sulfate binding, as shown by far-UV CD spectroscopy FIG. 3: Scatchard plot analysis and equilibrium dissociation constants (Kd values) of WT MCP-1 (solid squares), Met-MCP-1 Y13A S21K (solid triangles) and Met-MCP-1 Y13A S21K Q23R (open circles) binding to unfractionated HS FIG. 4: Calcium influx assay induced by 20 nM wtMCP-1 and MCP-1 mutants (20 nM each) on THP-1 cells. The changes in fluorescence emission at 495 nm due to calcium mobilization induced by addition of chemokines are displayed: wtMCP-1 (A), Met-MCP-1 Y13A S21K (B), Met-MCP-1 Y13A S21K Q23R (C) and Met-MCP-1 Y13A S21K Q23R V47K (D).

Figure 5:
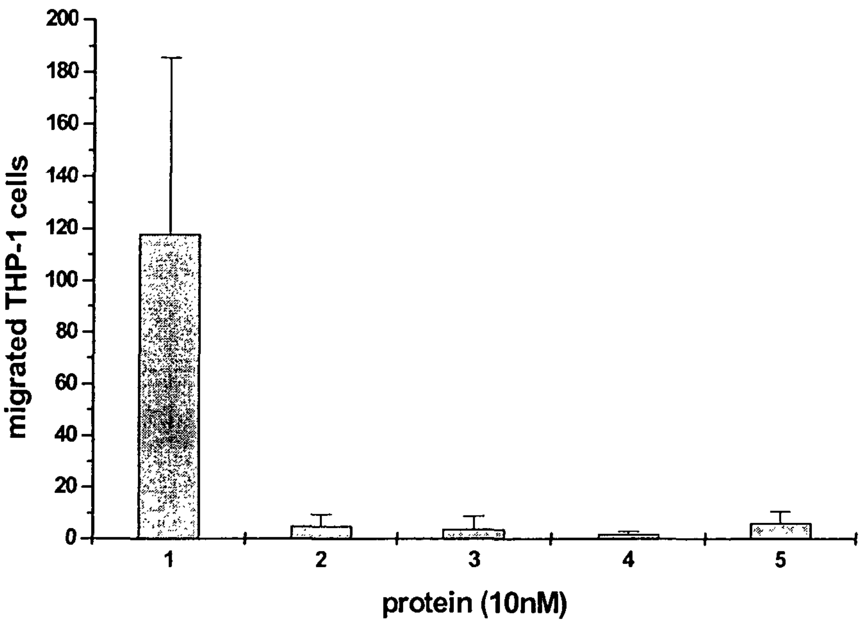

FIG. 5: Chemotaxis of THP-1 cells induced by wtMCP-1 and MCP-1 mutants at a concentration of 10 nM (error bars represent the SEM of three independent experiments). 1 wtMCP-1, 2 Met-MCP-1, 3 Met-MCP-1 Y13A S21K, 4 Met-MCP-1 Y13A S21K Q23R, 5 Met-MCP-1 Y13A S21K Q23R V47K.

Figure 6:
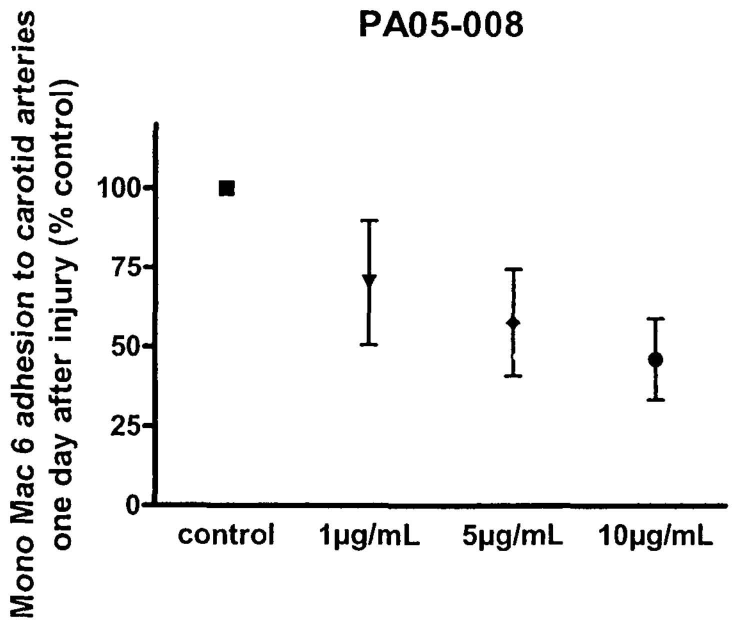

FIG. 6: Dose-dependent inhibition of monocyte adhesion/efflux by Met-MCP-1 Y13AS21KQ23R (described by the compound code PA05-008) as measured in a murine ex vivo carotide injury model.

Figure 7:
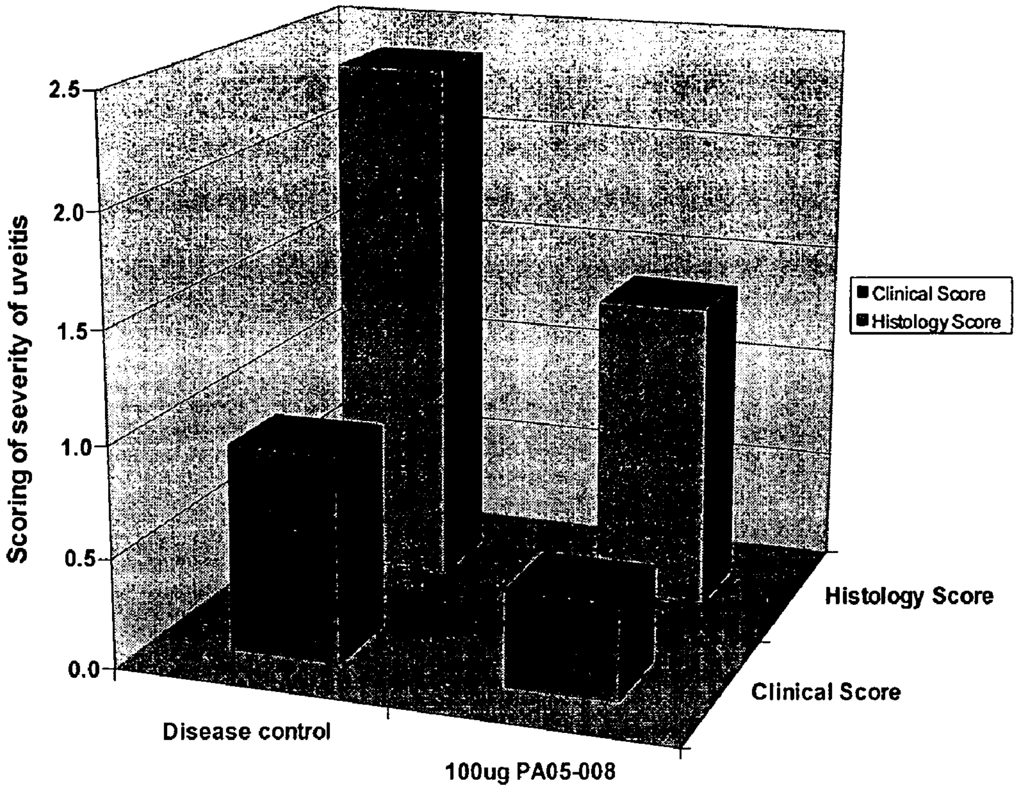

FIG. 7: Improvement of clinical and histological scores in a rat model of auto-immune uveitis after treatment with Met-MCP-1 Y13AS21KQ23R.

Figure 8:
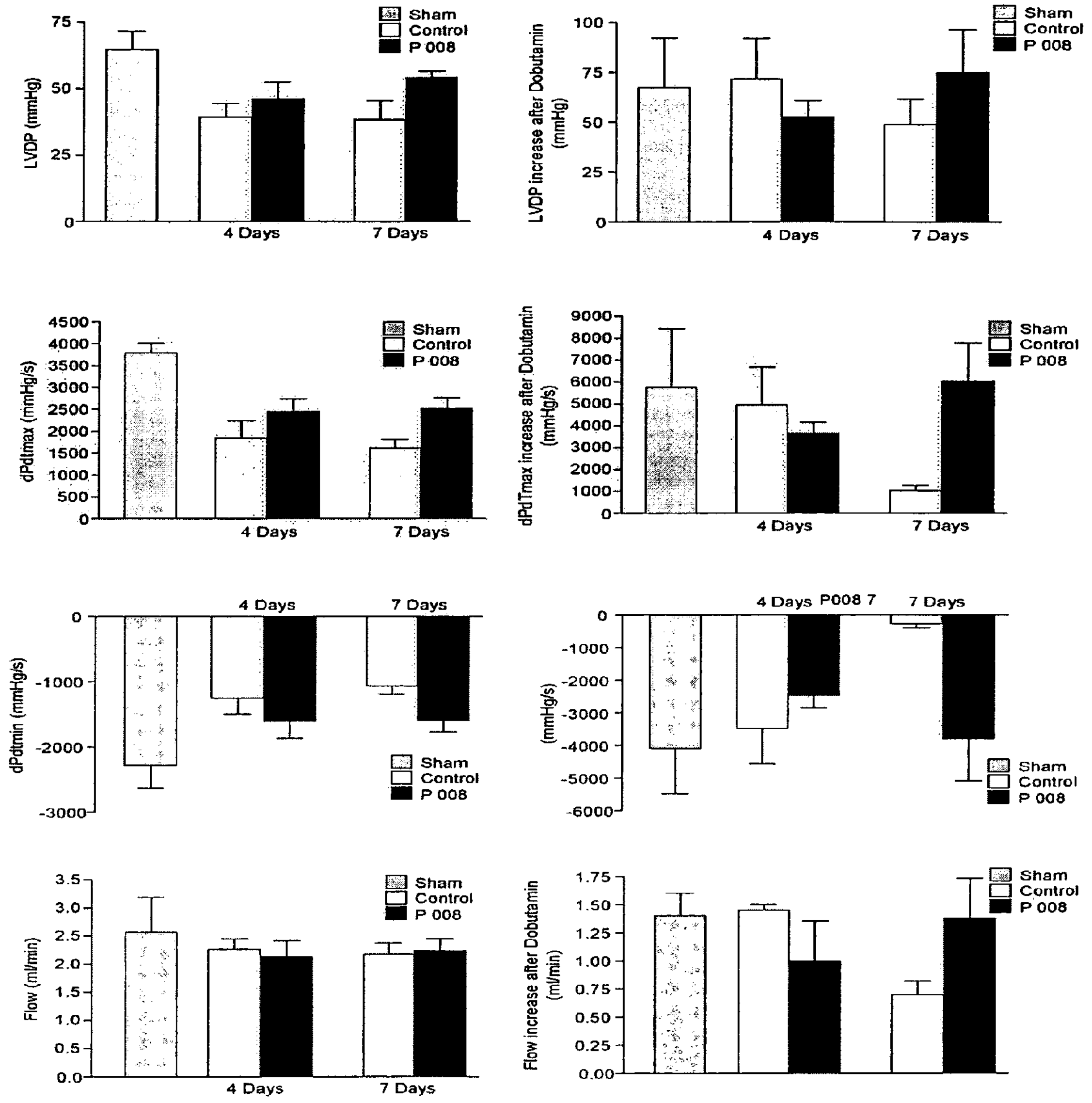
Figure 8:
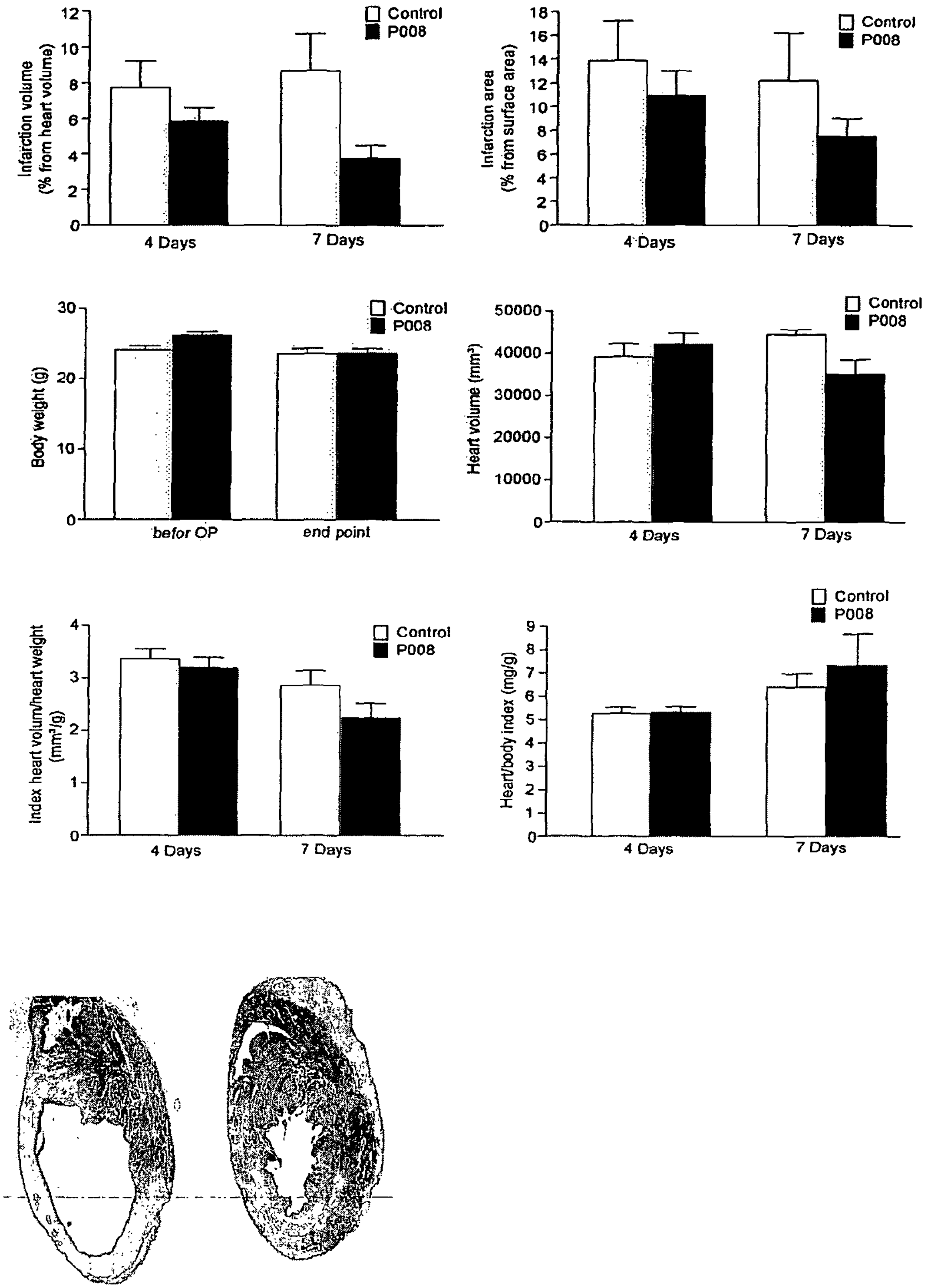

FIG. 8: Effect of Met-MCP-1 Y13AS21KQ23R (indicated as PA008) on ischemia reperfusion injury in a murine myocardial infarct model.

FIG. 9: Nucleotide sequences of MCP-1 Y13AS21 KV47K, MCP-1 Y13AS21KQ23R, MCP-1 Y13AS21KQ23RV47K All dimensions specified in this disclosure are by way of example only and are not intended to be limiting. Further, the proportions shown in the foregoing figures are not necessarily to scale.

It has been shown that increased GAG binding affinity can be introduced by increasing the relative amount of basic and/or electron donating amino acids in the GAG binding region (also described in WO 05/054285, incorporated in total herein by reference), leading to a modified protein that acts as competitor with natural GAG binding proteins. This was particularly shown for interleukin-8. The specific location of GAG binding regions and their modification by selectively introducing at least two basic and/or electron donating amino acids was not disclosed for MCP-1 protein.

Additionally, the amino terminus of MCP-1 was found to be essential for chemokine signalling through its GPC receptor CCR2. In order to engineer an MCP-1-based CCR2 antagonist, others have engineered MCP-1 in a way to completely knock-out GAG binding and to leave CCR2 binding intact (WO03084993A1). By these means, it was intended to block MCP-1-mediated signalling by blocking the CCR2 receptor on neutrophils and to prevent attachment on the endothelium via the GAG chains. It was therefore not obvious to turn this approach around by blocking the GAG chains on the endothelium (by engineering higher GAG binding affinity) and to knock out the CCR2 binding of MCP-1.

The invention now provides a novel MCP1 mutant protein with increased GAG binding affinity and reduced GPCR activity compared to the wild type MCP1 protein, wherein a region of the MCP-1 protein is modified in a structure conserving way by insertion of at least one basic and/or electron donating amino acids or by replacement of at least two amino acids preferably within the native GAG binding site or within the structural vicinity of a native GAG binding site by at least two basic and/or electron donating amino acids.

According to a specific embodiment, the modified MCP-1 protein further comprises a further modification of at least one amino acid of the first 1 to 10 amino acids of the N-terminal region of said MCP-1 protein by addition, deletion and/or replacement of at least one amino acid residue.

If the native amino acids replaced by said basic or electron donating amino acids are basic amino acids, the substituting amino acids have to be more basic amino acids or comprise more or less structural flexibility compared to the native amino acid residue. Structural flexibility according to the invention is defined by the degree of accommodating to an induced fit as a consequence of GAG ligand binding.

According to a specific embodiment of the invention the native amino acids replaced by basic and/or electron donating amino acids are non-basic amino acids.

According to the definition as used in the present application MCP-1 mutant protein can also include any parts or fragments thereof that still show chemokine activity like monocyte or T-cell chemotaxis and Ca-release.

The term "vicinity" as defined according to the invention comprises amino acid residues which are located within the conformational neighbourhood of the GAG binding site but not positioned at the GAG binding sites. Conformational neighbourhood can be defined as either amino acid residues which are located adjacent to GAG binding amino acid residues in the amino acid sequence of a protein or amino acids which are conformationally adjacent due to three dimensional structure or folding of the protein.

The term "adjacent" according to the invention is defined as lying within the cut-off radius of the respective amino acid residues to be modified of not more than 20 nm, preferably 15 nm, preferably 10 nm, preferably 5 nm.

To be able to perform their biological function, proteins fold into one, or more, specific spatial conformations, driven by a number of non-covalent interactions such as hydrogen bonding, ionic interactions, Van der Waals' forces and hydrophobic packing. Three dimensional structure can be determined by known methods like X-ray crystallography or NMR spectroscopy.

Identification of native GAG binding sites can be determined by mutagenesis experiments. GAG binding sites of proteins are characterized by basic residues located at the surface of the proteins. To test whether these regions define a GAG binding site, these basic amino acid residues can be mutagenized and decrease of heparin binding affinity can be measured. This can be performed by any affinity measurement techniques as known in the art.

Rational designed mutagenesis by insertion or substitution of basic or electron-donating amino acids can be performed to introduce foreign amino acids in the vicinity of the native GAG binding sites which can result in an increased size of the GAG binding site and in an increase of GAG binding affinity.

The GAG binding site or the vicinity of said site can also be determined by using a method as described in detail in U.S. Pat. No. 6,107,565 comprising:

(a) providing a complex comprising the protein and the GAG ligand molecule, for example heparan sulfate (HS), heparin, keratin sulfate, chondroitin sulfate, dermatan sulfate and hyaluronic acid etc. bound to said protein;

(b) contacting said complex with a cleavage reagent like a protease, e.g. trypsin, capable of cleaving the protein, wherein said GAG ligand molecule blocks protein cleavage in a region of the protein where the GAG ligand molecule is bound, and whereby said protein is cleaved in regions that are not blocked by said bound GAG ligand molecule; and (c) separating and detecting the cleaved peptides, wherein the absence of cleavage events in a region of the protein indicates that said GAG ligand molecule is bound to that region. Detection can be for example by LC-MS, nanoHPLC-MS/MS or Mass Spectrometric Methods.

A protocol for introducing or improving a GAG binding site is, for example, partially described in WO 05/054285 and can be as follows:

- Identify a region of the protein which is involved in GAG binding
- Design a new GAG binding site by introducing (replacement or insertion) at least one basic or electron donating amino acids, preferably Arg, Lys, His, Asp and Gin residues at any position or by deleting at least two amino acids which interfere with GAG binding
- Check the conformational stability of the resulting mutant protein in silica
- Provide the wild type protein cDNA (alternatively: purchase the cDNA)
- Use this as template for PCR-assisted mutagenesis to introduce the above mentioned changes into the amino acid sequence
- Subclone the mutant gene into a suitable expression system (prokaryotic or eukaryotic dependent upon biologically required post-translational modifications)
- Expression, purification and characterization of the mutant protein in vitro Criterion for an increased GAG binding affinity: $K_d^{GAG}$(mutant)≦10 uM.
- Check for structural conservation by far-UV CD spectroscopy or 1-D NMR spectroscopy.

A deviation of the modified structure as measured by far-UV CD spectroscopy from wild type MCP-1 structure of less than 30%, preferably less than 20%, preferably less than 10% is defined as structure conserving modification according to the invention. According to an alternative embodiment, the structure conserving modification is not located within the N-terminus of the MCP1 protein.

The key residues relating to the GAG binding domain of wtMCP-1 are S21, Q23 and/or V47. According to the invention, the MCP-1 mutant protein may contain at least two amino acid modifications within at least two amino acid residues at positions 21, 23 and/or 47.

The modifications can be, for example, a substitution of, or replacement by, at least two basic or electron donating amino acids. Electron donating amino acids are those amino acids which donate electrons or hydrogen atoms (Droenstedt definition). Specifically, these amino acids can be N or Q. Basic amino acids can be selected from the group consisting of R, K and H.

According to a further embodiment of the invention, R at amino acid position 18 can by modified by K, and/or K19 position can be modified by R and/or P8 can be modified by any amino acid substitution to at least partially decrease receptor binding of the modified MCP-1.

Alternatively, the MCP-1 mutant protein of the invention is characterized in that Y at position 13 is further substituted by any amino acid residue, preferably by A.

Y13 and R18 were shown to be also critical residues for signalling, and the replacement of these residues by other amino acid residues gave rise to a protein unable to induce chemotaxis. Two-dimensional 1H-15N HSQC spectra recorded on both deletion and substitution MCP-1 variants revealed that these mutations do not generate misfolded proteins (Chad D. Paavola et al., J. Biol. Chem., 273 (50), 33157-33165 (1998)).

Furthermore, the N-terminal methionine reduces the binding affinity of MCP-1 for CCR2 on THP-1 cells (Hemmerich S. et al, Biochemistry 38 (40), 13013-13025 (1999)) so that the chemotactic potency of [Met]-MCP-1 is approximately 300-fold lower than of the wild type (Jarnagin K. et al., Biochemistry 38, 16167-16177 (1999)). This is in contrast to the potent receptor antagonist [Met]-RANTES which does not induce chemotaxis but binds with high affinity to the receptor.

Therefore, according to an alternative embodiment of the invention, the MCP-1 mutant protein may contain an N-terminal Met. MCP-1 variants retaining the N-terminal methionine appear to have an increased apparent affinity for heparin (Lau E. K. et al., J. Biol. Chem. 279 (21), 22294-22305 (2004)).

According to the present invention, the N-terminal region of the wild type MCP-1 region that can be modified comprises the first 1 to 10 N-terminal amino acids. The inventive MCP-1 mutant protein can also have the N-terminal amino acid residues 2-8 deleted. Truncation of residues 2-8 ([1+9−76] hMCP-1) produces a protein that cannot induce chemotaxis.

Specifically, MCP-1 mutant protein can be selected from the group of Met-MCP-1 Y13A S21K V47K, Met-MCP-1 Y13A S21K Q23R and Met-MCP-1 Y13A S21K Q23R V47K.

In order to knock out GPCR activity and at the same time to improve affinity for GAGs, minimizing the number of modifications as far as possible, site-directed MCP-1 mutants were designed using bioinformatical and biostructural tools. This means, since the structure of wtMCP-1 is known, mutants were rationally designed. This means for knocking-in higher GAG binding affinity, that more GAG binding sites are introduced into the already existing GAG binding domain by replacing amino acids which are not directly involved in GAG binding, which are structurally less important, and which are solvent exposed by vicinity to basic amino acids such as K or R. By doing so, special attention was drawn to conserving the specific GAG interaction sites of MCP-1, i.e. those amino acids responsible for hydrogen bonding and van der Waals contacts with the GAG ligand, as well as the overall fold of the chemokine to preserve the ability of the chemokine to penetrate chemokine networks which relies on protein-protein interactions contained in the surface of MCP-1.

The amino acid sequence of the modified MCP-1 molecule can be described by the general formula:

$(M)_n Q(PDAINA(Z1))_m$VTCC(X1)NFTN (Z2)(Z3)I (X2)V(X3)RLASYRRITSSKCP KEAVIFKTI (X4) AKEICADPKQ KWVQDSMDHL DKQTQTPKT wherein Z1 is selected from the group of P and A, G, L, preferably it is A,
wherein Z2 is selected from the group of R and K,
wherein Z3 is selected from the group of K and R,
wherein X1 is selected from the group consisting of Y and A, preferably it is A,
wherein X2 is selected from the group consisting of S, R, K, H, N and Q, preferably it is K,
wherein X3 is selected from the group consisting of R, K, H, N and Q, preferably it is R,
wherein X4 is selected from the group consisting of V, R, K, H, N and Q, preferably it is K,
and wherein n and/or m can be either 0 or 1 and wherein at least two of positions X2, X3 or X4 are modified.

A further aspect of the present invention is an isolated polynucleic acid molecule which codes for the inventive protein as described above.

Specifically, an isolated polynucleic acid molecule comprising a nucleotide sequence of SEQ ID No. 7, SEQ ID No. 8 or SEQ ID No. 9 or at least part thereof is covered, too.

The polynucleic acid may be DNA or RNA. Thereby the modifications which lead to the inventive MCP-1 mutant protein are carried out on DNA or RNA level. This inventive isolated polynucleic acid molecule is suitable for diagnostic methods as well as gene therapy and the production of inventive MCP-1 mutant protein on a large scale.

Alternatively, the isolated polynucleic acid molecule hybridizes to the above defined inventive polynucleic acid molecule under stringent conditions. Depending on the hybridisation conditions, complementary duplexes form between the two DNA or RNA molecules, either by perfectly matching or also by comprising mismatched bases (see Sambrook et al., Molecular Cloning: A laboratory manual, $2^{nd}$ ed., Cold Spring Harbor, N.Y. 1989). Probes greater in length than about 50 nucleotides may accomplish up to 25 to 30% mismatched bases. Smaller probes will accomplish fewer mismatches. The tendency of a target and probe to form duplexes containing mismatched base pairs is controlled by the stringency of the hybridization conditions which itself is a function of factors, such as the concentrations of salt or formamide in the hybridization buffer, the temperature of the hybridization and the post-hybridization wash conditions. By applying well known principles that occur in the formation of hybrid duplexes, conditions having the desired stringency can be achieved by one skilled in the art by selecting from among a variety of hybridization buffers, temperatures and wash conditions. Thus, conditions can be selected that permit the detection of either perfectly matching or partially matching hybrid duplexes. The melting temperature (Tm) of a duplex is useful for selecting appropriate hybridisation conditions. Stringent hybridization conditions for polynucleotide molecules over 200 nucleotides in length typically involve hybridizing at a temperature 15-25° C. below the melting temperature of the expected duplex. For olignucleotide probes over 30 nucleotides which form less stable duplexes than longer probes, stringent hybridization usually is achieved by hybridizing at 5 to 10° C. below the Tm. The Tm of a nucleic acid duplex can be calculated using a formula based on the percent G+C contained in the nucleic acids and that takes chain lengths into account, such as the formula $$Tm = 81.5 - 16.6(\log [NA^+]) + 0.41(\%G+C) - (600/N),$$

where N=chain length.

A further aspect relates to a vector comprising an isolated DNA molecule according to the present invention, as defined above. The vector comprises all regulatory elements necessary for efficient transfection as well as efficient expression of proteins. Such vectors are well known in the art and any suitable vector can be selected for this purpose.

A further aspect of the present invention relates to a recombinant cell which is transfected with an inventive vector as described above. Transfection of cells and cultivation of recombinant cells can be performed as well known in the art. Such a recombinant cell as well as any descendant cell therefrom comprises the vector. Thereby, a cell line is provided which expresses the MCP-1 mutant protein either continuously or upon activation depending on the vector.

A further aspect of the invention relates to a pharmaceutical composition comprising a MCP-1 mutant protein, a polynucleic acid or a vector according to the present invention, as defined above, and a pharmaceutically acceptable carrier. Of course, the pharmaceutical composition may further comprise additional substances which are usually present in pharmaceutical compositions, such as salts, buffers, emulgators, coloring agents, etc.

A further aspect of the present invention relates to the use of the MCP-1 protein, a polynucleic acid or a vector according to the present invention, as defined above, in a method for either in vivo or in vitro inhibiting or suppressing the biological activity of the respective wild type protein. As mentioned above, the MCP-1 mutant protein of the invention will act as an antagonist whereby the side effects which occur with known recombinant proteins will not occur with the inventive MCP-1 mutant protein. In this case this will particularly be the biological activity involved in inflammatory reactions.

Therefore, a further use of the MCP-1 protein, a polynucleic acid or a vector according to the present invention, as defined above, is in a method for producing a medicament for the treatment of an inflammatory condition. In particular, it will act as antagonist without side effects and will be particularly suitable for the treatment of inflammatory diseases or conditions, either of chronic or acute nature. Therefore, a further aspect of the present invention is also a method for the treatment of inflammatory diseases or allergic conditions, wherein the MCP-1 mutant protein according to the invention, the isolated polynucleic acid molecule or vector according to the present invention or a pharmaceutical preparation according to the invention is administered to a patient.

More specifically, the inflammatory diseases or allergic conditions are respiratory allergic diseases such as asthma, allergic rhinitis, COPD, hypersensitivity lung diseases, hypersensitivity pneumonitis, interstitial lung disease, (e.g. idiopathic pulmonary fibrosis, or associated with autoimmune diseases), anaphylaxis or hypersensitivity responses, drug allergies and insect sting allergies; inflammatory bowel diseases, such as Crohn's disease and ulcerative colitis; spondyloarthropathies, scleroderma; psoriasis and inflammatory dermatoses such as dermatitis, eczema, atopic dermatitis, allergic contact dermatitis, uticaria; vasculitis; autoimmune diseases with an aetiology including an inflammatory component such as arthritis (for example rheumatoid arthritis, arthritis chronica progrediente, psoriatic arthritis and arthritis deformans) and rheumatic diseases, including inflammatory conditions and rheumatic diseases involving bone loss, inflammatory pain, hypersensitivity (including both airways hypersensitivity and dermal hypersensitivity) and allergies. Specific auto-immune diseases include autoimmune hematological disorders (including e.g. hemolytic anaemia, aplastic anaemia, pure red cell anaemia and idiopathic thrombocytopenia), systemic lupus erythromatosus, polychondritis, Wegener granulomatosis, dermatomyositis, chronic active hepatitis, myasthenia gravis, psoriasis, Steven-Johnson syndrome, autoimmune inflammatory bowel disease (including e.g. ulcerative colitis, Crohn's disease and Irritable Bowel Syndrome), autoimmune thyroiditis, Behcet's disease, endocrine opthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, and glomerulonephritis (with and without nephrotic syndrome, e.g. including idiopathic nephrotic syndrome or minimal change nephropathy); graft rejection (e.g. in transplantation including heart, lung, combined heart-lung, liver, kidney, pancreatic, skin, or corneal transplants) including allograft rejection or xenograft rejection or graft-versus-host disease, and organ transplant associated arteriosclerosis; atherosclerosis; cancer with leukocyte infiltration of the skin or organs; stenosis or restenosis of the vasculature, particularly of the arteries, e.g. the coronary artery, including stenosis or restenosis which results from vascular intervention, as well as neointimal hyperplasia; and other diseases or conditions involving inflammatory responses including ischemia reperfusion injury, hematologic malignancies, cytokine induced toxicity (e.g. septic shock or endotoxic shock), polymyositis, dermatomyositis, and granulomatous diseases including sarcoidosis.

Preferably, the inflammatory disease is selected form the group comprising rheumatoid arthritis, uveitis, inflammatory bowel disease, myocardial infarction, congested heart failure or ischemia reperfusion injury.

The following examples describe the invention in more detail without limiting the scope of the invention.

EXAMPLES

The carotide injury model as well as the animal models used for the present invention were performed in the laboratories of Prof. Christian Weber (Universitätsklinikum Aachen).

Structural Analysis of MCP-1 Mutants Upon GAG Binding

Analysis of secondary structural elements of MCP-1 mutants by far-UV CD spectroscopy showed that the overall ratio of alpha/beta/turns was conserved during protein design. Furthermore, protein unfolding studies showed that particularly Met-MCP-1 Y13AS21KQ23R exhibited very similar unfolding transition parameters compared to the wild type protein, indicating similar stability of these protein variants. Also the small secondary structural change induced by HS binding found for wtMCP-1 was reproduced in the MCP-1 mutants (as exemplified by the comparison of wtMCP-1 and Met-MCP-1 Y13AS21KQ23R in FIG. 1). However, the stability of both proteins was significantly improved in the presence of HS as determined by temperature-induced unfolding studies. This means that contrary to other chemokines, HS impacts the fold of MCP-1 variants stronger than their secondary structure. This may be partly due to the elongated, partially unstructured form of MCP-1 in the absence of GAGs which experiences a structure-induction upon GAG binding, leading to a more compact fold and, thus, to greater stability.

Increase in GAG Binding Affinity

Figure 3:
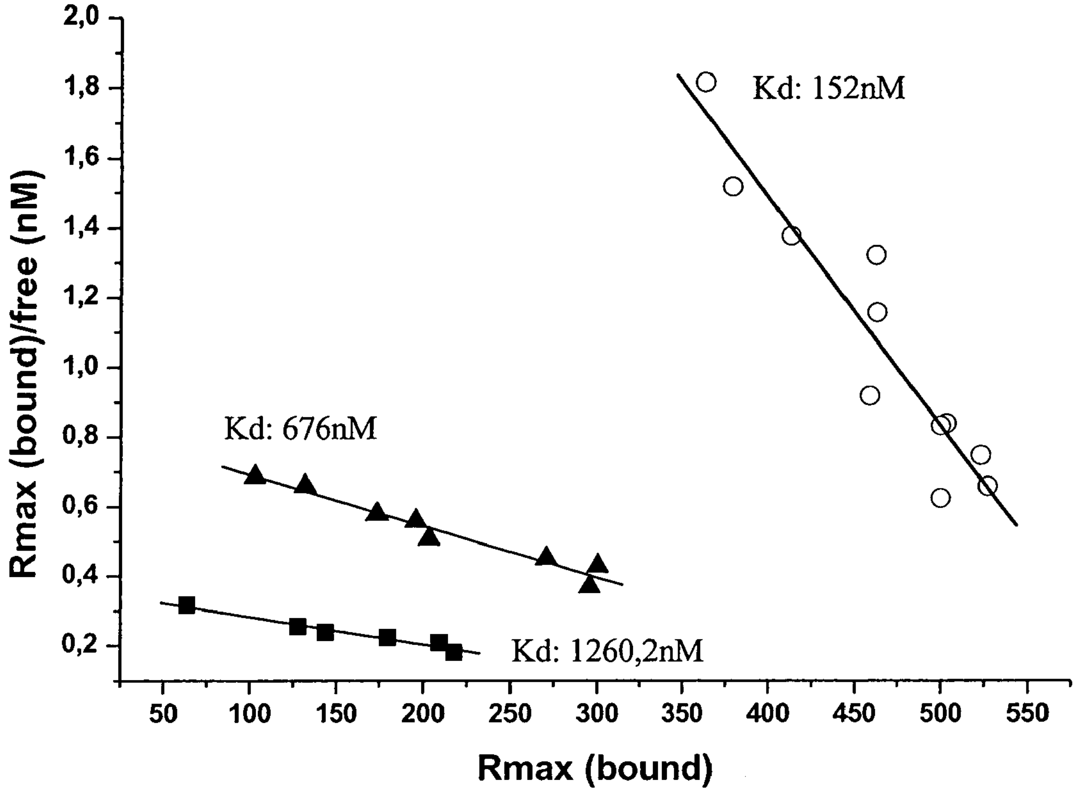

We have determined the increased GAG binding affinity by surface plasmon resonance (SPR) using a Biacore 3000 system. The immobilization of biotinylated HS onto a streptavidin coated CM4 sensor chip was performed according to an established protocol (28). The actual binding interactions were recorded at 25° C. in PBS pH 7.4 containing 0.01% (v/v) P20 surfactant (BIAcore AB). 2.5 min injections of different protein concentrations at a flow rate of 60 μl/min were followed by 5 min dissociation periods in buffer and a pulse of 1M NaCl for complete regeneration. The maximum response signals of protein binding to the HS surface, corresponding to the plateaus of the respective sensograms, were used for Scatchard plot analysis and the calculation of equilibrium dissociation constants (Kd values). In FIG. 3 the Scatchard plots of wtMCP-1 and two mutants are displayed. wtMCP-1 gave a Kd value of 1.26 μM, Met-MCP-1 Y13A S21K yielded 676 nM, and Met-MCP-1 Y13A S21K Q23R gave 152 nM. This means that in the latter mutant the affinity for HS has been improved by a factor of >8. The Met-MCP-1 Y13AS21KV47K mutant did not exhibit any improvement in affinity for the natural HS ligand.

Knock-Out of GPCR Activity

Figure 4:
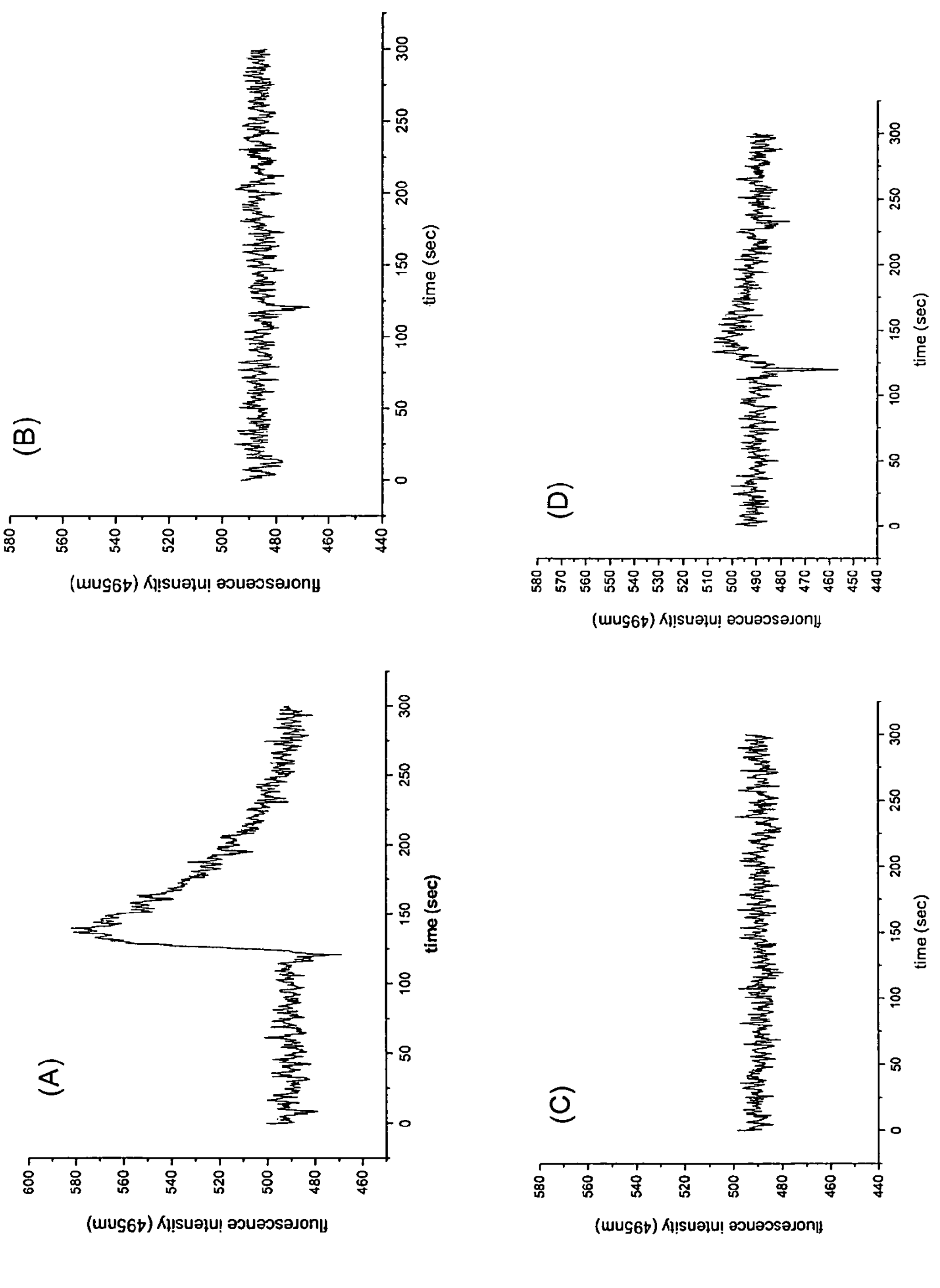

In order to obtain dominant-negative MCP-1 mutants, the GPCR activity of MCP-1 has been knocked out in addition to the improved GAG binding affinity. This was done by replacing the tyrosine residue at position 13 by an alanine residue and by keeping the N-terminal methionine residue. This led to a complete knock-out of MCP-1-related CCR2 activity, as exemplified by the complete absence of Ca influx and Thp-1 chemotaxis in the case of the Met-MCP-1 Y13A S21K Q23R mutant (FIGS. 4 & 5). The inability of this mutant to activate its high-affinity GPC receptor on target monocyte cells is expected to lead, in combination with the increased GAG binding affinity, to a potent inhibitor of MCP-1 activity in vivo.

Inhibition of Cell Migration

The effect of Met-MCP-1 Y13A S21K Q23R on monocyte migration was investigated in an ex vivo model. For this purpose, apolipoprotein E-deficient (Apoe)−/− mice were subjected to wire-induced endothelial denudation injury after 1 week of atherogenic diet (1). After 24 hours carotid arteries were isolated for ex vivo perfusion as described (1). Carotid arteries were preperfused at 5 μl/min with Met-MCP-1 Y13A S21K Q23R at a concentration of 1, 5 or 10 μg/ml for 30 min. Mono Mac 6 cells ($1'10^6$/ml) were labeled with calcein-AM, washed twice and perfused through the carotid artery. Adhesive interactions with the injured vessel wall were recorded using stroboscopic epifluorescence illumination (Drelloscop 250, Drello) and an Olympus BX51 microscope after 10 min of perfusion. By this means, a concentration dependent inhibition of monocyte adhesion by Met-MCP-1 Y13AS21KQ23R was observed (see FIG. 6).

Inhibition/Improvement of Auto-Immune Uveitis

Lewis rats were immunized into both hind legs with a total volume of 200 μl emulsion containing 15 μg PDSAg (retinal peptide) in complete Freund's adjuvant, fortified with Mycobacterium tuberculosis strain H37RA (BD, Heidelberg, Germany) to a final concentration of 2.5 mg/ml. 100 μg Met-MCP-1Y13AS21-KQ23R mutant dissolved in 0.5 ml PBS (or PBS only as control) was applied i. p. daily from day 1 after active immunization until day 19. The time course of disease was determined by daily examination of animals with an opthalmoscope. Uveitis was graded clinically as described (Gong J. H. and Clark-Lewis I., J. Exp. Med. 181 (2), 631-640 (1995))) and the average clinical score of all eyes is shown per group and day. As can be seen from FIG. 7, the Met-MCP-1 Y13AS21KQ23R mutant had a significant impact on the progression of the disease. Since uveitis is characterized by occular accumulation of T-cells and monocytes which finally lead to blindness, the therapeutic effect of Met-MCP-1 Y13AS21KQ23R can be assigned to its inhibition of the migration of CCR2-activated leukocytes which mainly constitute monocytes and basophils.

Inhibition/Improvement of Myocardial Infarction

C57/B6 mice were intubated under general anaesthesia (100 mg/kg ketamine and 10 mg/kg xylasine, intraperitoneal) and positive pressure ventilation was maintained with oxygen and isofluran 0.2% using a rodent respirator. Hearts were exposed through a left toracotomy and MI was produced by suture occlusion of the left anterior descending artery (LAD) over a two mm silicon tube. The suture was opened after 30 min by cutting the silicon tube and reperfusion was re-established. In sham-operated mice, the suture was left open during the same time. The muscle layer and skin incision were closed with a silk suture. Animal experiments were approved by local authorities and complied with German animal protection law.

Met-MCP-1 Y13AS21KQ23R was dissolved in PBS at 100 μg/ml. Mice were treated intraperitoneally with 100 μl each during ischemia (10 min after ligation), 2 hours after reperfusion, and every day until the end point. Control mice were treated in the same way with vehicle.

At indicated time points, mice were anesthetized and the heart function was analyzed using a Langendorff apparatus (Hugo Sachs Elektronik-Harvard Apparatus) and HSE Isoheart software under constant perfusion pressure (100 mmHg) and electrical stimulation to assure a constant heart rate (600 bpm). The coronary flow, developed pressure, the increase (dP/dtmax) and decrease (dP/dtmin) in left ventricular pressure were measured without or with dobutamin (300 μmol in bolus). The measured parameters are displayed in FIG. 8 (upper-panel). At the end, the hearts were fixed in distension with 10% formalin and cut into 5 μm serial slices.

Serial sections (10-12 per mouse, 400 μm apart, until mitral valve) were stained with Gomori's 1 step trichrome stain. The infarction area was determined on every section using Diskus software (Hilgers) and express as percent from total left ventricular volume (see FIG. 8, lower panel).

The invention claimed is:

1. An MCP-1 mutant protein with increased GAG binding affinity and reduced GPCR activity compared to wild type human MCP-1 protein, wherein the MCP-1 protein is modified by replacement of two non-basic amino acids with two basic amino acids selected from the group consisting of arginine (R), lysine (K), and histidine (H), wherein the non-basic amino acids being replaced comprise the amino acids at positions 21 and 23 of the wild type human MCP-1 protein as set forth in SEQ ID NO:1.

2. The MCP-1 mutant protein of claim 1, wherein the non-basic amino acids being replaced by basic amino acids further comprise the non-basic amino acid at position 47 of the wild type human MCP-1 protein as set forth in SEQ ID NO:1, wherein the amino acid at position 47 is replaced by a basic amino acid selected from the group consisting of arginine (R), lysine (K), and histidine (H).

3. A pharmaceutical composition which comprises a protein according to claim 1 and a pharmaceutically acceptable carrier.

4. The MCP-1 mutant protein of claim 1, wherein serine (S) at amino acid position 21 is replaced by K and glutamine (Q) at amino acid position 23 is replaced by R.

5. The MCP-1 mutant protein of claim 1, wherein S at amino acid position 21 is replaced by K, Q at amino acid position 23 is replaced by R, and valine (V) at amino acid position 47 is replaced by K.

6. The MCP-1 mutant protein of claim 1, wherein the non-basic amino acid at amino acid position 21 is replaced by R.

7. The MCP-1 mutant protein of claim 1, wherein the non-basic amino acid at amino acid position 21 is replaced by K.

8. The MCP-1 mutant protein of claim 1, wherein the non-basic amino acid at amino acid position 21 is replaced by H.

9. The MCP-1 mutant protein of claim 1, wherein the non-basic amino acid at amino acid position 23 is replaced by R.

10. The MCP-1 mutant protein of claim 1, wherein the non-basic amino acid at amino acid position 23 is replaced by K.

11. The MCP-1 mutant protein of claim 1, wherein the non-basic amino acid at amino acid position 23 is replaced by H.

12. The MCP-1 mutant protein of claim 2, wherein the non-basic amino acid at amino acid position 47 is replaced by R.

13. The MCP-1 mutant protein of claim 2, wherein the non-basic amino acid at amino acid position 47 is replaced by K.

14. The MCP-1 mutant protein of claim 2, wherein the non-basic amino acid at amino acid position 47 is replaced by H.

15. A pharmaceutical composition which comprises a protein according to claim 2 and a pharmaceutically acceptable carrier.

* * * * *